United States Patent [19]

Rapp et al.

[11] 4,335,966

[45] Jun. 22, 1982

[54] METHOD OF PREPARING CONCRETE MIXTURES

[75] Inventors: Joachim Rapp, Weingarten; Peter Bittmann, Gaggenau, both of Fed. Rep. of Germany

[73] Assignee: Elba-Werk Maschinen-Gesellschaft mbH & Co., Ettlingen, Fed. Rep. of Germany

[21] Appl. No.: 218,202

[22] Filed: Dec. 19, 1980

[30] Foreign Application Priority Data

Dec. 22, 1979 [DE] Fed. Rep. of Germany ....... 2952124

[51] Int. Cl.³ .......................... B28C 5/00; B28C 7/04
[52] U.S. Cl. ........................................... 366/2; 366/40
[58] Field of Search ...................... 366/2, 3, 8, 10, 16, 366/49

[56] References Cited

U.S. PATENT DOCUMENTS

| | | |
|---|---|---|
| 1,225,129 | 5/1917 | Hochstrasser .......................... 366/2 |
| 1,854,180 | 4/1932 | Cross ....................................... 366/2 |
| 3,480,261 | 11/1969 | Eirich ..................................... 366/7 |
| 3,593,966 | 7/1971 | Munroe ................................. 366/40 |

Primary Examiner—Edward J. McCarthy
Attorney, Agent, or Firm—Montague & Ross

[57] ABSTRACT

A process for adding water to a concrete mix wherein, after addition of an initial quantity of water to bring a particular concrete mix to or close to a so-called zero consistency, the set point consistency is reached by the one-shot addition of the balance of the water determined from stored empirical and interpolated data based upon measuring consistency and water addition values. The method has the advantage that the establishment of a zero value consistency by the addition of water to the dry mix or a mix of unknown moisture content permits the consistency measurement at this point to be easily carried out by indirect electrical techniques.

5 Claims, 3 Drawing Figures

METHOD OF PREPARING CONCRETE MIXTURES

CROSS REFERENCE TO RELATED APPLICATION

The present application relates to the commonly assigned copending application Ser. No. 105,734 filed Dec. 20, 1979 and entitled "Method of and Apparatus for Feeding water to a Concrete Mix".

FIELD OF THE INVENTION

Our present invention relates to a method of preparing concrete mixtures and, more particularly, to a method of adding water to, or controlling the addition of water to, a concrete mix in the preparation of pourable concrete mixtures.

BACKGROUND OF THE INVENTION

Concrete mixes generally comprise a hydraulic cement, e.g. a Portland cement, a coarse aggregate in the form of gravel and a fine aggregate such as sand, which must be combined with water to form a pourable concrete mixture capable of setting up to considerable hardness. The cement, sand and gravel together form the so-called dry mix in spite of the fact that at least the aggregate (sand and/or gravel) may contain varying amounts of intrinsic moisture depending upon mode of preparation, method of storage and even weather conditions.

It is known to indirectly measure the consistency of a concrete mixture by electrical resistance methods and to empirically determine the water quantities which must be added to bring the ultimate concrete preparation or mixture to a desired or set point consistency.

In general, the consistency measurement is carried out on the concrete mix by determining the electrical resistance thereof and tubulated values of this consistency versus water additions for a given set point consistency, can be consulted to allow the preparation of concrete mixtures with the desired consistency. These tabulated values permit concrete mixes of various compositions and characteristics to be handled with comparative ease.

The water is generally supplied in increments (pulsed water feed) until the desired consistency value is reached by simply determining values of the water present for certain actual value consistencies and the set point (final) consistency for the respective mixes.

These techniques have the disadvantage that the time to completion of preparation of the mix is excessive, generally because of the time required for the incremental addition of water, and/or because the measurement by electrical resistance techniques of the actual-value consistency takes place in a consistency range at which the measurements are unreliable or nonreproducible, usually because of the high degree of dryness of the mix.

In fact, it has been found that varying concrete compositions in the presence of the small amount of moisture generally encountered when the actual value consistency is measured, require various measurement techniques or manipulation to obtain any significant results whatsoever. Relatively dry mixes, for example, necessitate determinations of specific electrical resistance while more moist mixes require determination of power consumption of the mixer drive in the measuring methods deemed optimal heretofore (see the aforementioned copending application). Obviously, earlier techniques are time-consuming and require complex and diverse apparatus and application to various concrete compositions.

OBJECTS OF THE INVENTION

It is, therefore, the principal object of the present invention to provide an improved method of preparing concrete mixtures by the controlled addition of water to the dry mix, whereby the disadvantages of earlier systems can be obviated.

Another object of our invention is to provide an improved method of controlling the addition of water to a concrete mix such that the ultimate mixture can be prepared in a shorter time and with greater ease and reliability than hitherto.

It is also an object of this invention to simplify a method of adding water to a concrete mix, especially so as to optimize the quality of the product and minimize the mixing time while allowing a single measurement technique to be used for mixes of a wide variety of compositions and intrinsic moistures.

SUMMARY OF THE INVENTION

These objects and others which will become apparent hereinafter are attained, in accordance with the present invention, in a method of adding water to a concrete mix or controlling the addition of water to a concrete mix which comprises initially bringing each mix, regardless of its composition and initial water content, substantially to a zero consistency level in which the consistency may be readily measured, e.g. by electrical resistence techniques, by the addition of water and, in a second step, supplying the water required to bring the mix to the set point consistency from the zero consistency.

It will be apparent that this approach eliminates problems with measurement reliability because all mixes are brought to a consistency value which allows a single measurement technique to be utilized, whereupon the tabulated values of water required for the set point consistency can be consulted and interpolated, if necessary, to give the quantity of water which, in a single shot, can be added to the mix to bring the latter to the set point consistency.

Advantageously, the method comprises the following steps:

(a) In an initial process step and using the techniques of the aforementioned application, for a variety of concrete mix compositions, an initial quantity of water is supplied, generally in a relatively large quantity by comparison to the maximum intrinsic moisture content of the mix, and then additional but smaller quantities of water are added with measurement of the consistency value for each water addition;

(b) In the next step, values for concrete consistency and the corresponding absolute quantity of water added are recorded (tabulated) after each addition of water;

(c) for each subsequent concrete charge:

($\alpha$) a predetermined relatively large second quantity of water is supplied which is larger than the initial quantity of water, ($\beta$) the actual value consistency of the mixture is determined, ($\gamma$1) the values of the concrete consistency flanking the measured actual value consistency are determined in the table, (γ2) by interpolation, a tabulated concrete consistency corresponding to the measured actual value consistency is ascertained, (δ1) the concrete consistency values for the desired or set point consistency are determined in the table, (δ2) a tabulated set point value is interpolated from the two latter values and the corresponding water quantity is determined, (ε) the difference of the total water values for the tabulated total water quantity corresponding to the actual value consistency and for the tabulated set point value consistency is taken and the water deficiency determined; and (d) the water deficiency as thus determined is added in a single shot.

In this embodiment the measurement of the actual value consistency of the mixture is determined after addition of the second prewater quantity and the residual water for the zero point consistency and the set point consistency are added simultaneously and in a single step or shot.

BRIEF DESCRIPTION OF THE DRAWING

The above and other objects, features and advantages of the present invention will become more readily apparent from the following description, reference being made to the accompanying drawing in which.

SPECIFIC DESCRIPTION

Wherever, in the following description, reference is made to consistency measurement, one of the techniques described in our copending application identified above may be used and wherever reference is made to tables or tabulated values, the electronic or automatic storage and information retrieval systems of that application may be employed. In other words, the stored or tabulated values may be stored in and retrieved from the memory of the computer which may have a keyboard or other terminal facility for recording in the memory the consistency and water values as there described. Alternatively, using analog/digital conversion and analog detection of consistency values and quantities of water added, the inputs to the memory may be automatically read into the memory and the mix compositions introduced into the memory by a keyboard. Finally, determination of the differences and any interpolation may all be carried out automatically by the computer of that application.

Figure 1:
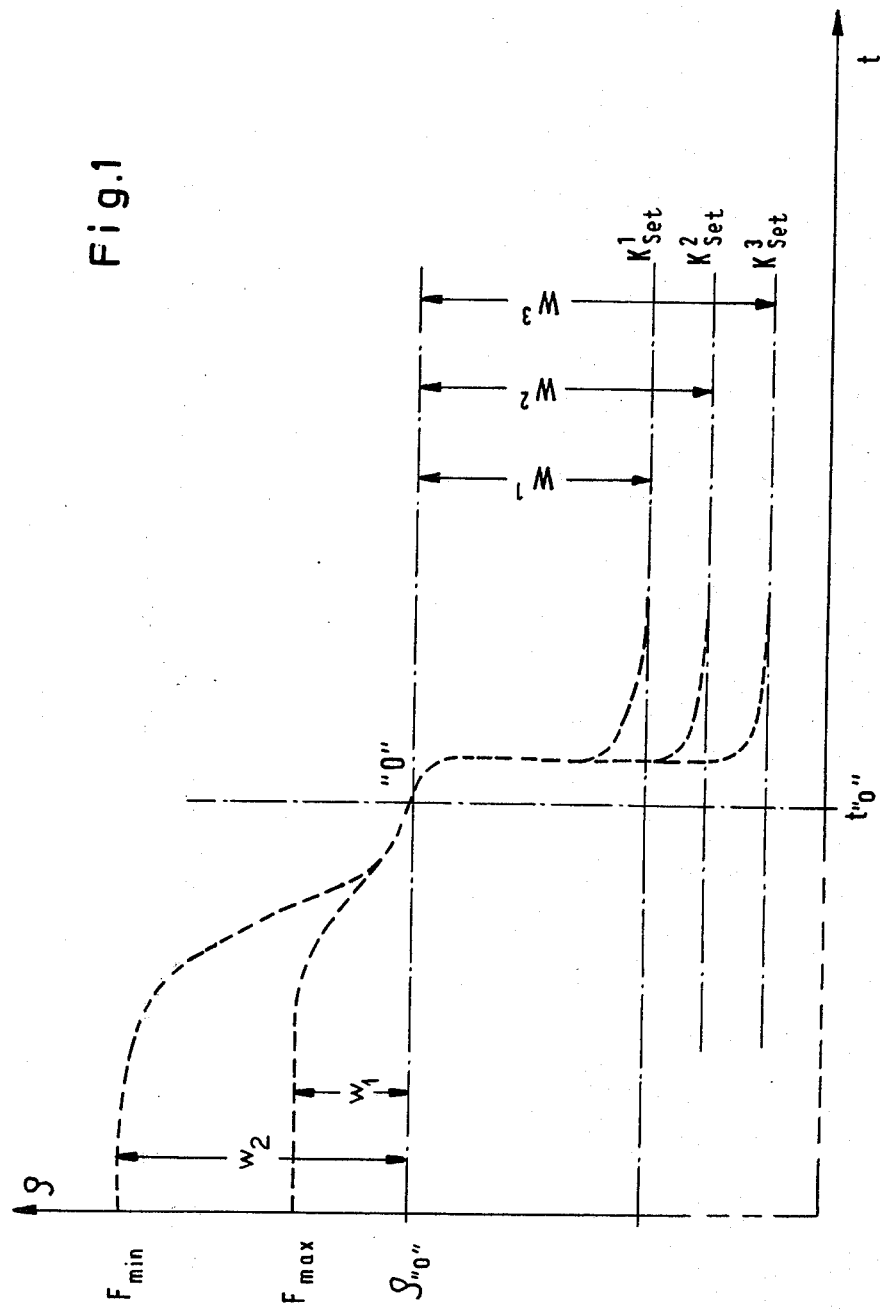
FIG. 1 is a diagram illustrating one embodiment of the invention.
Figure 2:
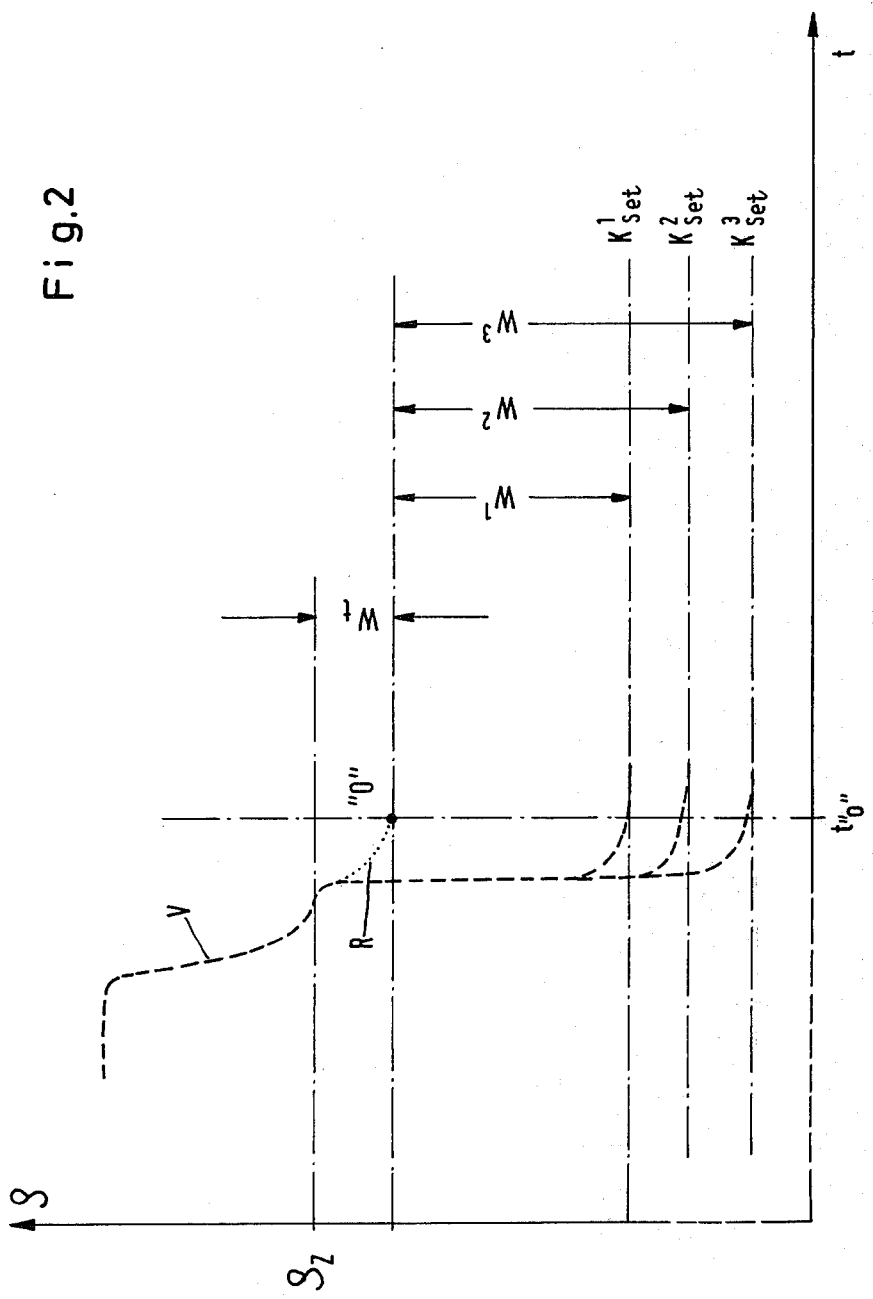
FIG. 2 is a diagram illustrating another embodiment thereof.

The diagrams of FIGS. 1 and 2 have plotter along the abscissa the mixing time parameter t while the ordinate displays measured values corresponding to consistency values.

Referring to FIG. 1, it can be seen that the zero consistency "0" is a fictitious value which is established to conform to certain boundary conditions:

Firstly, the zero consistency value must be able to be attained by the addition of water. This can be seen in FIG. 1 in which initial water additions $w_1$ and $w_2$ are required. The zero level consistency point should lie at the lower end of the scale of different concrete consistency.

Secondly, this point should lie in a region in which consistency values can be readily and reproducibly measured, i.e. somewhere below $F_{max}$.

Finally, it must lie in the region in which the water content of the concrete is greater than the highest possible intrinsic moisture content of the aggregate. If the intrinsic moisture content is defined by $F_{max}$, therefore, the water content at the zero consistency point "0" is the instrinsic water content+$w_1$.

These boundary conditions thus allow at the zero level consistency, reliable electric resistance measurements.

The process represented in FIG. 1 can be carried out as follows:

In an initial stage of the process, for various set point consistency $K^1_{set}$, $K^2_{set}$ and $K^3_{set}$ the water additions $W^1$, $W^2$ and $W^3$ are determined, e.g. by the use of a standard consistency and as determined by accurate slump tests and carefully controlled water addition.

The results are tabulated in the manner described.

For each subsequent mix, water is added in one or more doses to the zero point consistency which is easily measured and which can automatically control the addition of water. At this point, the stored values of the set point consistency are consulted and a value obtained by interpolation between set point consistency, corresponding to the particular set point consistency desired. Interpolation is made between the two corresponding water values $W^1$ and $W^2$ or $W^2$ and $W^3$ and the corresponding quantity of water is added in a single dose. After the requisite mixing time, the concrete mixture is complete.

A variant is represented in FIG. 2.

This process utilizes principles set forth in our copending application and the curve portion V represents the point reached in the sequence (c), (d), in which a second prewater mix is supplied. The actual consistency value corresponding to a resistance value $\rho$ is determined and after interpolation between tabulated values, the residual water quantity $W_t$ to bring the curve to the zero level consistency over the imaginary section R, plus the interpolated quantity between $W^1$ and $W^2$ or $W^2$ and $W^3$ is established for the set point consistency. The makeup water $W_t$ plus the quantity required from the zero consistency to the set point value is then added in a single shot.

Figure 3:
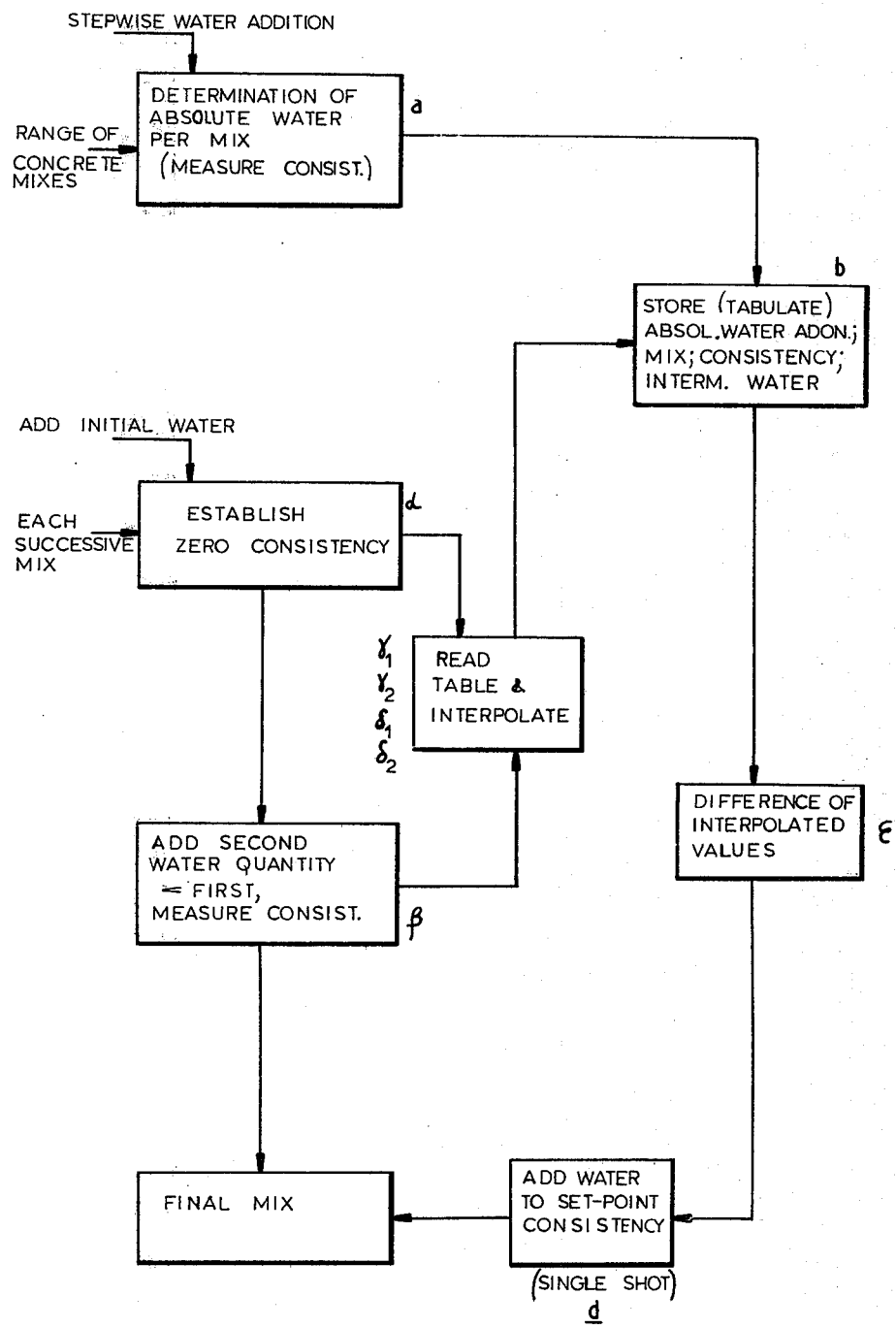
FIG. 3 is a flow diagram illustrating steps and information transfer process in the system of the present invention.

In FIG. 3, we have represented the method of the invention in block diagram form. Initially one determines the absolute water quantity for a range of concrete mixes by stepwise water addition, measuring the consistency with each addition, the values then being stored or tabulated. For each additional mix an initial water quantity is added with measurement of the consistency to establish the zero consistency, or a second quantity of water less then that of the initial quantity is added and consistency can be measured. The table or storage is read and interpolated and the interpolated value or the difference as described controls the addition of water in a single shot to the final mix.

We claim:

1. A method of controlledly preparing a concrete mixture comprising the steps of:

(a) establishing a zero consistency for concrete mixes at a water content thereof in excess of the intrinsic water content of aggregates to be used in such mixes and adapted to be formed by the addition of water thereto whereby the water content of a mix at said zero consistency is less than the water content of the mix at a plurality of set point consistencies;

(b) establishing the quantity of water required to bring a mix from said zero consistency to each of said set point consistencies; and (c) for each subsequent mix, ($c_1$) adding water thereto until as determined by consistency measurement, the consistency thereof reaches said zero consistency, and ($c_2$) thereafter adding in a single shot the balance of the water required to bring each mix at zero consistency to a corresponding set point consistency.

2. The method defined in claim 1 wherein the quantity of water required to bring a mix at zero consistency to each of a number of set point consistencies is tabulated and the quantity of water added in step ($c_2$) is determined by interpolation from tabulated values.

3. The method defined in claim 1 or claim 2 wherein in step ($c_1$), water is added incrementally to bring each subsequent mix to said zero consistency.

4. The method defined in claim 1 or claim 2 wherein said zero consistency is established in step ($c_1$) by adding a first prewater quantity to the respective mix, thereafter adding a second prewater quantity less than the first to said mix, and determining the quantity of water required thereafter to reach said zero consistency, the latter quantity of water being supplied to said mix concurrently with the water supplied in step ($c_2$).

5. A method of controlledly adding water to a concrete mix which comprises the steps of:

(a) for a plurality of concrete consistencies determining the consistency and quantity of water required to bring a concrete mix thereto and recording consistency and added-water quantities in tabular form;

(b) establishing a zero-consistency readily measurable for concrete mixes and corresponding to a water content above the maximum intrinsic moisture content of aggregates of such mixes but less than the water contents of set point values of concrete consistencies, the tabulated data including the quantity of water required to bring each mix at a given set point consistency from the zero consistency; and (c) for each subsequent mix:

($c_1$) adding an initial relatively large quantity of water thereto, ($c_2$) adding a relatively small second quantity of water for each mix to bring the consistency thereof into the region of said zero consistency, ($c_3$) measuring the consistency of the latter mix and determining from the tabulated data by interpolation between two recorded consistency values, the quantity of water required to bring the consistency of each mix to the zero consistency, ($c_4$) interpolating between two set point consistencies for a desired set point consistency of the mix and establishing the quantity of water required to bring the mix from the zero consistency to the desired set point consistency, and ($c_5$) adding the quantities of water established in step ($c_3$) and ($c_4$) to the mix in a single dose.

* * * * *